United States Patent [19]
Broadbent et al.

[11] 3,932,394
[45] Jan. 13, 1976

[54] ANTIVIRAL COMPLEX

[75] Inventors: Douglas Broadbent; Harold George Hemming; Barrie Hesp, all of Macclesfield, England

[73] Assignee: Imperial Chemical Industries Limited, London, England

[22] Filed: Aug. 28, 1973

[21] Appl. No.: 392,354

[30] Foreign Application Priority Data
Sept. 14, 1972 United Kingdom............... 42694/72

[52] U.S. Cl........ 260/243 R; 424/246; 260/268 PC; 260/239.3 P; 195/81; 260/236.5
[51] Int. Cl.².......................................... C07D 285/00
[58] Field of Search ................................ 260/243 R

[56] References Cited
UNITED STATES PATENTS 3,701,774  10/1972  Miller et al. ........................ 260/243
3,745,158  7/1973  De Long et al. .................... 260/243

*Primary Examiner*—John M. Ford
*Attorney, Agent, or Firm*—Cushman, Darby & Cushman

[57] ABSTRACT

The disclosure relates to a process for producing an antiviral complex by cultivation of *Sirodesmium diversum*, to novel components of the complex and to derivatives thereof having antiviral activity, to processes for their manufacture, to pharmaceutical compositions containing the complex, the novel components or their derivatives, and to a method of producing an antiviral effect.

2 Claims, No Drawings

ANTIVIRAL COMPLEX

This invention relates to a novel antiviral complex, its production and its components.

According to the invention there is provided a process for producing an antiviral complex which comprises the cultivation of an antiviral complex producing strain of *Sirodesmium diversum* in an aqueous nutrient medium containing a source of assimilable carbon and a source of assimilable nitrogen, extraction of the culture filtrate with a substantially water immiscible organic solvent, and evaporation of the extract to dryness.

A suitable strain of the fungus is for example *Sirodesmium diversum* (Cooke) Hughes originating from the Commonwealth Mycological Institute, located at Ferry Lane, Kew, England and catalogued as C.M.I. 102,519.

The culture grows well on conventional mycological agar media, and after 6 days the colonies show a central area of sporing mycelium surrounded by a zone of immature hyphae which may be both aerial and submerged, or primarily submerged. This zone is not coloured. The sporing area is normally dark brown, with spore-bearing cells arising from the agar and from aerial growth, which can be quite vigorous - as for instance on malt agar, or which can be sparse as for instance on Czapek-Dox agar.

The spores, which are produced from unspecialised branches of conidiophores, are seen in long, rarely branched, chains. They are amerospores and didymospores phargmospores are rare) which mature basipetally. When mature, the spores are coarsely warted with a brown/yellow cell wall usually quite thick, but with occasional thin places. Amerospores are globose 10(9–11)$\mu$m in diameter, while the didymospores are subcylindric with a constriction at the septum 18(15–22) × 10(9–15)$\mu$m (they look essentially like two amerospores which have failed to separate).

A suitable source of assimilable carbon is, for example, a polyhydric alcohol, for example sucrose, glucose, lactose, glycerol or mannitol; a source of polymerised carbohydrate, for example starch; a naturally-occurring or synthetic oil or fat; or mixtures of two or more of the abovementioned substances. The carbon source is generally present in the medium within the range of 0.1 to 30 percent by weight and preferably within the range of 2 to 8 percent by weight.

A suitable source of assimilable nitrogen is an inorganic source or an organic source. it may conveniently be provided in the form of, for example, a nitrate of an alkali metal or an alkaline earth metal, or an ammonium salt of an inorganic acid or an organic acid, for example sodium, potassium, calcium or ammonium nitrate or ammonium tartrate, ammonium sulphate or ammonium phosphate. It may also be provided in the form of an amino-acid, for example glycine, a seed meal, for example cottonseed meal, or corn steep liquor, peptone, urea, a yeast extract or a meat extract. Mixtures of two or more of the abovementioned substances may be used. The nitrogen source is generally present in the medium in an amount such that there is present between 0.001 and 1.0 percent, and preferably between 0.01 and 0.5 percent of elementary nitrogen in the medium.

The medium usually contains smaller quantities of essential elements such as phosphorus (for example as potassium dihydogen phosphate or di-ammonium hydrogen phosphate), magnesium (for example as magnesium sulphate or magnesium carbonate), sulphur (for example as a sulphate) and potassium (for example as potassium chloride or potassium carbonate) and minute quantities of so-called trace elements such as iron, manganese, zinc, molybdenum or copper.

As a suitable aqueous nutrient medium there may be mentioned, for example, the medium known as Czapek-Dox.

The cultivation of the organism may be carried out within the temperature range of 15° to 35°C., preferably at a temperature of about 25°C.

A suitable substantially water-immiscible organic solvent is, for example, chloroform, ethyl acetate, toluene or diethyl ether, and of these chloroform is preferred.

The antiviral complex has been found to comprise eight new compounds which possess antiviral properties. Thus according to a further feature of the invention there are provided eight new antiviral poducts isolated from the antiviral complex obtained from the culture filtrate of *Sirodesmium diversum* and identified as Sirodesmins A,B,C,D, E,F,G and H respectively.

Sirodesmin A has the structure given in formula I in which $R^1$ is acetyl, $R^2$ is hydrogen and *n* is 2:-

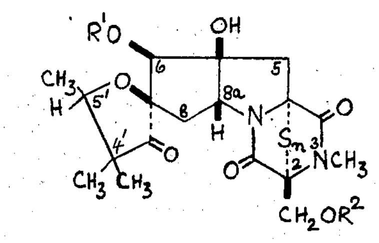

I

The stereochemistry illustrated is the relative stereochemistry.

Sirodesmin B has the structure I in which $R^1$ is acetyl, $R^2$ is hydrogen and n is 4 and Sirodesmin C has the structure I in which $R^1$ is acetyl, $R^2$ is hydrogen and n is 3.

The 3 compounds, Sirodesmins A, B and C, incorporate an epi-(n)-thiadioxopiperazine ring system. Other molecules possessing the epi-(n)-thiadioxopiperazine ring system and having antiviral properties are known, for example Aranotin and Apoaranotin (U.K. Pat. No. 1,238,327) and Gliotoxin, but these known compounds are either not as active as the compounds of the present invention, or have a lower therapeutic ratio as hereinafter defined.

Treatment of the antiviral complex with sulphur dioxide gives rise to another compound having antiviral properties, Sirodesmin J. Thus according to a further feature of the invention, we provide a further compound Sirodesmin J.

The Sirodesmins A,B,C,D,E,F,G,H and J are identifiable by the following characteristics:-

SIRODESMIN A

Molecular formula $C_{20}H_{26}N_2O_8S_2$

Analysis. Found C,49.7; H,5.4; N,5.8; S,12.8% Calc. for $C_{20}H_{26}N_2O_8S_2$;C,49.4; H,5.4; N,5.8; S,13.2%

Mass Spectrum. No parent is shown but a strong peak at $(M\text{-}S_2)^+$. Found m/e 422,1731, $C_{20}H_{26}N_2O_8$ requires m/e 422.1689. On silylation with trimethylsilyl imidazole (benzene, 60°, 3 hr.) there is formed a bis-trimethylsilyl derivative. No parent ion is seen in the mass spectrum of this derivative but a weak peak corresponding to $(M-CH_3)^+$ is seen at m/e 615.1689, $C_{25}H_{39}N_2O_8S_2Si_2$ requires 615.1686.

Acetylation. Treatment of Sirodesmin A with acetic anhydride in pyridine for 1 week at 22°C. gives a bis-acetate, m.p. 186°–189°C. Found C,50.5; H, 5.3; N, 4.9%. $C_{24}H_{30}N_2O_{10}S_2$ requires C, 50.7; H,5.2; N, 4.9%. Mass spectrum highest peak $(M-S_2)^+$ at m/e 506.1871. $C_{24}H_{30}N_2O_{10}$ requires m/e 506.1901.

Treatment with Sirodesmin A with acetic anhydride in pyridine for 1 hour at 22°C. gives a monoacetate. Found C,49.9; H, 5.3; N, 5.3; S,11.7%; $C_{22}H_{28}N_2O_9S_2$ requires C,50.0; H, 5.3; N,5.2; S,12.1%. Mass spectrum a small peak for $(M-S)^+$ at m/e 496 and a strong peak for $(M-S_2)^+$ at m/e 464.

Hydrolysis of Sirodesmin A with 0.1N methanolic HCl gives Desacetylsirodesmin A, m.p. 198°–201°C. Found C,48.4; H,5.6; N, 6.0; S,14.3%; $C_{18}H_{24}N_2O_7S_2$ requires C, 48.8; H,5.6; N,6.3; S,14.4%. Mass spectrum. No parent ion is shown but a strong peak for $(M-S_2)^+$ at m/e 380.

Treatment of Sirodesmin A with triphenylphosphine in chloroform gives a monosulphide. Found, C,52.7; H,5.7; N,5.8; S,7.1%; $C_{18}H_{26}N_2O_8S$ requires C,52.9; H, 5.8; N, 6.2; S,7.0%. Mass spectrum. Molecular ion seen in m/e 454.

SIRODESMIN B

Molecular formula $C_{20}H_{26}N_2O_8S_4$. Analysis Found C,43.4; H,4.9; N, 4.9; S, 22.8%. $C_{20}H_{26}N_2O_8S_4$ requires C, 43.6; H, 4.8; N, 5.1; S,23.3%. Mass spectrum. No parent is shown but a strong peak for $(M-S_4)^+$ at m/e 422. The spectrum is virtually identical with that of Sirodesmin A. On silylation with bis-trimethylsilyl trifluoroacetamide (benzene, 50°, 3 hr.) there is formed a bis-trimethylsilyl derivative. No parent is seen in the mass spectrum of this derivative but a weak peak corresponding to $[M-(S+CH_3)]^+$ is seen at m/e 647.1445 $C_{25}H_{39}N_2O_8S_3Si_2$ requires m/e 647.1407.

SIRODESMIN C

Molecular formula $C_{20}H_{26}N_2O_8S_3$. Analysis. Found C, 46.3; H, 5.1; N,5.5; S,18.0%; $C_{20}H_{26}N_2O_8S_3$ requires C, 46.3; H, 5.0; N, 5.4; S, 18.5%. Mass spectrum. Strong peak corresponding to $(M-S_3)^+$ at m/e 422 $(C_{20}H_{26}N_2O_8)$.

SIRODESMIN D

Molecular formula $C_{20}H_{26}N_2O_8S_x$ in which x is probably 4. Mass spectrum. No parent ion is shown but a strong peak for $(M-S_x)^+$ at m/e 422.

SIRODESMIN E

Molecular formula $C_{20}H_{26}N_2O_8S_x$ in which x is probably 3. Mass spectrum. No parent ion is shown but a strong peak for $(M-S_x)^+$ at m/e 422.

SIRODESMIN F

Molecular formula $C_{20}H_{26}N_2O_8S_x$ in which x is probably 3. Mass spectrum. No parent ion is shown but a strong peak for $(M-S_x)^+$ at m/e 422.

SIRODESMIN G

Molecular formula $C_{20}H_{26}N_2O_8S_2$. Analysis. Found C, 49.7; H, 5.4; N, 5.7; S,12.6%. Calculated for $C_{20}H_{26}N_2O_8S_2$, C, 49.4; H, 5.4; N, 5.8; S,13.2%. Mass spectrum. No parent ion is shown but a strong peak for $(M-S_2)^+$ at m/e 422. Hydrolysis: Treatment of Sirodesmin G with 0.1N methanolic HCl gave Desacetylsirodesmin G, m.p. 195°–196.5°C. Found C, 48.4; H, 5.5; N, 6.5; S, 14.6%. Calculated for $C_{18}H_{24}N_2O_7S_2$, C, 48.8; H,5.5; N, 6.3; S,14.4%. Mass spectrum. No parent ion, but a strong peak for $(M-S_2)^+$ at m/e 380. Acetylation. Treatment of Sirodesmin G with acetic anhydride in pyridine for 9 days at ambient temperature gives Sirodesmin G bisacetate, m.p. 159°–159.5°C.

SIRODESMIN H

Molecular formula $C_{20}H_{26}N_2O_8S_x$. Mass spectrum. No parent ion, but a strong peak for $(M-S_x)^+$ at m/e 422.

SIRODESMIN J

Molecular formula $C_{20}H_{26}N_2O_8S_2$. Analysis. Found C, 49.8; H, 5.5; N, 5.5%. Calculated for $C_{20}H_{26}N_2O_8S_2$, C, 49.4; H, 5.4; N, 5.8%. Mass spectrum. No parent ion but a strong peak for $(M-S_2)^+$ at m/e 422 and a weak peak for $(M-S)^+$ at m/e 454.

The Sirodesmins A,B,C,D,E,F,G,H and J and their derivatives are separated by analtyical thin layer chromatography on silica gel G.F. After development the plates are sprayed with chromic acid solution and then heated; the spots first appear yellow, then black. The $R_f$ values, using three different solvent systems, are as follows:-

| Compound | Toluene; Ethyl Acetate 1:2 | Chloroform: methanol: formic acid 95:4:1 | Chloroform: ethyl acetate 1:1 |
|---|---|---|---|
| Sirodesmin A | 0.23 | 0.35 | 0.19 |
| Sirodesmin B | 0.07 | 0.24 | 0.06 |
| Sirodesmin C | 0.17 | 0.29 | 0.14 |
| Sirodesmin D | 0.31 | 0.29 | 0.25 |
| Sirodesmin E | 0.36 | 0.33 | 0.27 |
| Sirodesmin F | 0.42 | 0.35 | 0.34 |
| Sirodesmin G | 0.38 | 0.39 | 0.32 |
| Sirodesmin H | 0.23 | 0.28 | 0.17 |
| Sirodesmin J | 0.38 | 0.35 | 0.28 |
| Desacetyl-sirodesmin A | 0.23 | 0.24 | 0.15 |
| Sirodesmin A bisacetate | 0.39 | 0.51 | 0.36 |
| Desacetyl-sirodesmin G | 0.33 | 0.27 | 0.23 |
| Sirodesmin G bisacetate | 0.52 | 0.55 | 0.49 |
| Sirodesmin A monoacetate | 0.31 | 0.45 | 0.26 |
| Sirodesmin monosulphide | 0.24 | 0.29 | 0.19 |

The Sirodesmins A-H are separated by high pressure liquid chromatography. Using a Du Pont 820 Liquid Chromatograph with an E.T.H. Permaphase (1 m. ×2.1 m.m. internal diameter) having as mobile phase a gradient of 0 to 1.25% redistilled ethanol in 2,2,4-trimethylpentane in 50 minutes, and at a pressure of 2000 p.s.i., the following retention times were recorded:-

| Compound | Retention Time (minutes) |
|---|---|
| Sirodesmin G | 15.5 |
| Soridesmin E | 23.5 |
| Sirodesmins A + D | 30.0 |
| Sirodesmin C | 35.0 |
| Sirodesmin H | 40.0 |
| Sirodesmin B | 44.0 |
| Sirodesmin F | 49.0 |

The Sirodesmins are most readily identified by examination of their N.M.R. spectra. The figures in the following tables provide the relevant assignments for the protons of Sirodesmins A,B,C,D,E,F,G,H and J when examined on a Varian HA100 N.M.R. spectrophotometer, in deuterochloroform as solvent except where otherwise indicated, using tetramethylsilane as an internal standard ($\tau = 10.0$). A bis-urethane is made in the N.M.R. sample tube by addition of trichloroacetyl isocyanate. The carbon numbers referred to in the tables are those depicted in figure I.

Sirodesmin A

| Carbon No. | Substituent | Signal ($\tau$) | Coupling constant (Hz) | Bis-Urethane Signal ($\tau$) | Coupling constant (Hz) |
|---|---|---|---|---|---|
| 2 | CH$_2$OH | 5.72 | | 4.9 | |
| | | | | 5.10 | 12 |
| 3 | CH$_3$ | 6.86 | | 6.85 | |
| 5 | H | 6.86 | | 6.32 | |
| | | | 16 | | 16 |
| | H | 6.94 | | 6.52 | |
| 6 | H | 4.26 | | 4.32 | |
| 5' | H | 5.78 | | 5.84 | |
| | | | 7 | | 7 |
| | CH$_3$ | 8.71 | | 8.76 | |
| 4' | CH$_3$ | 8.98 | | 9.01 | |
| | CH$_3$ | 9.06 | | 9.09 | |
| 6 | CH$_3$CO.O | 7.90 | | 7.93 | |
| 8 | H | 7.44 | | 7.42 | |
| | | | 14* | | 14 |
| | H | 8.04 | | 7.98 | |
| 8a | H | 5.52 | | 5.10 | |

*Coupling constant with hydrogen at 8a position 8.5 Hz

Sirodesmin B

| Carbon No. | Substituent | Signal ($\tau$) | Coupling constant (Hz) | Bis-Urethane Signal ($\tau$) | Coupling constant (Hz) |
|---|---|---|---|---|---|
| 2 | CH$_2$OH | 5.88 | * | 5.16 | |
| 3 | CH$_3$ | 6.97 | | 6.90 | |
| 5 | H | 6.74 | | 6.33 | |
| | | | 15 | | 16 |
| | H | 7.32 | | 6.67 | |
| 6 | H | 4.46 | | 4.73 | |
| 5' | H | 5.84 | | 5.72 | |
| | | | 7 | | 7 |
| | CH$_3$ | 8.74 | | 8.77 | |
| 4' | CH$_3$ | 9.04 | | 8.98 | |
| | CH$_3$ | 9.08 | | 9.04 | |
| 6 | CH$_3$CO.O | 7.98 | | 7.86 | |
| 8 | H | 7.49 | | 7.47 | |
| | | | 14+ | | 14+ |
| | H | 8.14 | | 8.01 | |
| 8a | H | 5.24 | | 4.56 | |

*Coupling constant 12Hz on addition of D$_2$O
+Coupling constant with hydrogen at 8a position 9 Hz Sirodesmin C exists as a mixture of two conformers in solution at room temperature. This has a precedent in, for example, the trisulphide Sporidesmin E. Thus several signals are duplicated in the N.M.R. spectra of solutions of Sirodesmin C in benzene or tetrachloroethylene when measured at room temperature. The spectra are less complex when measured at higher temperatures.

SIRODESMIN C IN TETRACHLOROETHYLENE i. Room Temperature

| Carbon No. | Substituent | Signal ($\tau$) |
|---|---|---|
| 5' | CH$_3$ | 8.70, 8.76 |
| 4' | CH$_3$ | 9.01, 9.09 |
| 6 | CH$_3$CO.O | 8.00 |
| 3 | CH$_3$ | 6.78, 6.96 |
| 6 | H | 4.68, 4.93 | ii. 120°C.

The 5' and 4' methyl signals become much sharper, the two lines for 3-methyl become single line, and the two lines for 6-H become single broad line. Sirodesmin C urethane in tetrachloroethylene i. Room Temperature

| Carbon No. | Substituent | Signal ($\tau$) |
|---|---|---|
| 5' | CH$_3$ | 8.83, 8.86, 8.94 |
| 4' | CH$_3$ | 9.07, 9.15 |
| 6 | CH$_3$CO.O | 8.07 |
| | NH | 0.99, 1.03, 1.09, 1.21 | ii. 120°C.

Signals due to 5', 4' and 6-acetate methyls become very sharp and the urethane NH signals become two lines.

SIRODESMIN C IN BENZENE (D$_6$)

i. Room Temperature

| Carbon No. | Substituent | Signal ($\tau$) |
|---|---|---|
| 5' | CH$_3$ | 9.1, 9.06, 9.04, 9.00 |
| 4' | CH$_3$ | 9.25, 9.37, 9.41 |
| 6 | CH$_3$CO.O | 8.52 |
| 3 | CH$_3$ | 7.03, 7.13 |
| 6 | H | 4.23, 4.50 | ii. 78°C.

"Duplicated" signals clearly beginning to merge but the process is not complete.

Sirodesmin D

| Carbon No. | Substituent | Signal ($\tau$) | Coupling constant (Hz) |
|---|---|---|---|
| 3 | CH$_3$ | 6.92 | |
| 5 | H | 6.58 | |
| | | | 16 |
| | H | 7.24 | |
| 6 | H | 4.62 | |
| 6 | CH$_3$CO.O | 7.94 | |
| 8 | H | 7.35 | |
| | | | 14* |
| | H | 8.20 | |
| 8a | H | 5.39 | |
| 4' | CH$_3$ | 8.90 | |
| | CH$_3$ | 8.98 | |
| 5' | CH$_3$ | 8.77 | |
| | | | 7 |
| | H | 6.09 | |

*Coupling constant with hydrogen at 8a position 9 Hz.

Sirodesmin G

| Carbon No. | Substituent | Signal ($\tau$) | Coupling constant (Hz) |
|---|---|---|---|
| 2 | CH$_2$OH | 5.83 | |
| | CH$_2$OH | 6.53 | |
| 3 | CH$_3$ | 6.91 | |
| 5 | H$_2$ | 6.80 | |
| 6 | H | 4.50 | |
| 5' | H | 6.10 | |
| | | | 7 |
| | CH$_3$ | 8.78 | |
| 4' | CH$_3$ | 8.93 | |
| | CH$_3$ | 9.01 | |
| 6 | CH$_3$CO.O | 7.96 | |
| 8 | H | 7.29 | |
| | | | 14* |
| | H | 8.29 | |
| 8a | H | 5.72 | |

*Coupling constant with hydrogen at 8a position 9Hz.

The main n.m.r. resonances ($\tau$ values of $CDCl_3$ solution) of Sirodesmins E,F,H,J and Desacetylsirodesmin G are as follows:-

Sirodesmin E 9.02($CH_3$), 8.93($CH_3$), 8.95, 8.83, 8.77, 7.99($CH_3CO.O$), 6.96($NCH_3$), 6.79, 5.34.

Sirodesmin F 9.06($CH_3$), 9.00($CH_3$), 8.73($CH_3$), 7.93($CH_3CO.O$), 7.29, 6.95, 6.79($NCH_3$), 5.30.

Sirodesmin H 9.01($CH_3$), 8.93($CH_3$), 8.79($CH_3$), 7.98($CH_3CO.O$), 6.93($NCH_3$), 6.41, 5.25.

Sirodesmin J 9.03($CH_3$), 8.98, 8.94, 8.79, 8.73, 7.91($CH_3CO.O$), 7.88, 6.84($NCH_3$), 6.60, 5.11.

Desacetylsirodesmin G 9.01($CH_3$), 8.98($CH_3$), 8.77, 8.33, 7.38, 7.13, 6.87($NCH_3$), 6.80, 6.14, 5.4–5.9, 4.7–5.0.

INFRA-RED SPECTRA

The infra-red spectra of the Sirodesmins are very similar. The principal absorption maxima of compounds examined as dispersions in liquid paraffin are as follows:-

| Compound | Absorption (cm.$^{-1}$) | | | | | | | | | |
|---|---|---|---|---|---|---|---|---|---|---|
| Sirodesmin A | 3450 | 1765 1690 1395 1225 | 1112 | 1075 | 1045 | 1008 | 943 | 722 | | |
| Sirodesmin B | 3450 | 1765 1680 1375 1228 | 1118 | 1082 | 1045 | | 946 | 722 | | |
| Sirodesmin C | 3450 | 1760 1685 1375 1225 | | 1080 | 1045 | 1008 | 945 | 722 | | |
| Sirodesmin D | 3400 | 1750 1670 1375 1230 | 1153 | 1083 | 1045 | 1015 | | 721 | | |
| Sirodesmin E | 3450 | 1750 1675 1375 1230 | 1155 | 1083 | 1047 | 1012 | | 722 | | |
| Sirodesmin G | 3450 | 1750 1683 1375 1230 | 1155 | 1083 | 1047 | 1015 | | 722 | | |
| Sirodesmin J | 3450 | 1760 1680 1380 1235 | 1085 | 1047 | | | | 722 | | |
| Sirodesmin A monoacetate | 3500 | 1745 1675 1360 1210 | 1035 | | | | 937 | 725 | | |
| Sirodesmin A bisacetate | | 1760 1695 1380 1235 | 1082 | 1055 | | | 940 | | | |
| Desacetyl-sirodesmin A | 3500 | 1748 1675 1412 1390 | 1375 | 1355 | 1305 | 1265 | 1240 | 1210 | | |
| | 1130 | 1085 1050 1008 939 | 857 | 800 | 727 | | | | | |

The Sirodesmins A,B,C,D,E,F,G and H, may be isolated from the antiviral complex by chromatography, for example by a combination of column chromatography and preparative thin layer chromatography. Thus according to a further feature of the inventionn we provide a process for the isolation of Sirodesmin A which comprises subjecting the antiviral complex to chromatography.

As mentioned above, treatment of Sirodesmin A with methanolic HCl gives Desacetylsirodesmin A. Therefore according to a further feature of the invention we provide a desacetyl derivative of Sirodesmin A,B or C which has the formula I in which both $R^1$ and $R^2$ are hydrogen and n is 2,4 or 3 respectively.

As mentioned above, treatment of Sirodesmin G with methanolic HCl gives Desacetylsirodesmin G. Therefore according to a further feature of the invention we provide Desacetylsirodesmin G, having a melting point of about 195°–196.5°C. and having nuclear magnetic resonances indeuterochloroform solution at 9.01, 8.98, 8.77, 8.33, 7.38, 7.13, 6.87, 6.80, 6.14, 5.4–5.9 and 4.7–5.0$\tau$.

According to a further feature of the invention, we provide a process for the manufacture of the desacetyl derivative of Sirodesmin A,B,C or G which comprises treatment of an alcoholic solution of Sirodesmin A,B,C or G with an inorganic acid. The solvent is preferably an alcohol or aqueous alcohol, for example methanol or aqueous methanol, and the acid is preferably HCl.

As mentioned above, treatment of Sirodesmin A with acetic anhydride in pyridine for 1 hour gives a monoacetate. Therefore according to a further feature of the invention we provide Sirodesmin A monoacetate, Sirodesmin B monoacetate or Sirodesmin C monoacetate which has the formula I in which $R^1$ and $R^2$ are both acetyl and n is 2,4 or 3 respectively.

According to a further feature of the invention we provide a process for the manufacture of Sirodesmin A monoacetate, Sirodesmin B monoacetate or Sirodesmin C monoacetate which comprises treatment of a solution of Sirodesmin A,B or C with acetic anhydride or an acetyl halide, for example acetyl chloride, in a non-hydroxylic organic solvent for a period of between 15 minutes and 4 hours. The preferred conditions are treatment with acetic anhydride in pyridine solution for 1 hour.

As mentioned above, treatment of Sirodesmin A with triphenylphosphine in chloroform gives Sirodesmin A monosulphide. Therefore according to a further feature of the invention we provide Sirodesmin monosulphide which has the formula I in which $R^1$ is acetyl, $R^2$ is hydrogen and n is 1.

According to a further feature of the invention we provide a process for the manufacture of Sirodesmin monosulphide which comprises treatment of a solution of Sirodesmin A in an organic solvent with triphenylphosphine. The solvent may, for example, be toluene, benzene or chloroform, of which chloroform is preferred.

Sirodesmins B and C are both readily converted into Sirodesmin A by treatment with thionyl chloride in pyridine at 0°C. The conversion may be effected directly in the antiviral complex and this greatly facilitates the isolation of Sirodesmin A.

Thus according to a further feature of the invention there is provided a process for the manufacture of Sirodesmin A by treatment of Sirodesmin B and/or Sirodesmin C, or of the antiviral complex obtained from the culture filtrate, with thionyl chloride in an organic base as solvent at a temperature below room temperature.

Sirodesmin A is converted into a mixture of A,B and C by treatment with sulphur in pyridine at room temperature.

Thus according to a further feature of the invention, there is provided a process for the manufacture of Sirodesmins B and C by treatment of a solution of Sirodesmin A in an organic solvent with sulphur in the presence of an organic base. The organic base itself may act as solvent.

It can be seen that Sirodesmins A,B and C, their monoacetates, their desacetyl derivatives and Sirodesmin monosulphide are interconvertable. Therefore as a further feature of the invention there is provided a compound of the formula I wherein n is 1,2,3 or 4 and either $R^1$ is acetyl and $R^2$ is hydrogen or $R^1$ and $R^2$ are both hydrogen or both acetyl.

The complex obtained by extraction of the fungal broth, the new compounds Sirodesmins A,B,C,D,E,F and G isolated therefrom, Sirodesmin J, the desacetyl derivatives of Sirodesmins A and G, Sirodesmin A monoacetate and Sirodesmin monosulphide all possess antiviral activity in the presence of host cells, in particular they possess activity against rhinoviruses in the presence of human embryonic lung cells, and against Coxsackie A and B Echo viruses. The activity against rhinoviruses is measured essentially as follows:

Human embryonic lung cells are cultured in conventional manner on Eagle's Minimal Essential Medium with 1 percent calf serum added, in 3 inches × ½ inch glass tubes, and the tubes are incubated at 33°C. Eight groups of three such tubes per group are treated with test solutions of a test compound in the same medium, and containing respectively 200, 50, 12.5, 3.1, 0.8, 0.2, 0.05 and 0.00 $\mu$g. of test compound per ml. of test solution. Incubation at 33°C. is continued, and after 24 hours each tube is challenged with a dose of a rhinovirus, for example rhinovirus type 2, of 100 times the tissue culture 50 percent infectious dose. After a further 2 days of incubation at 33°C., each tube is assessed visually for a cytopathic effect caused by compound toxicity, which is a generalised cytopathic effect on the whole cell sheet, and for the cytopathic effect caused by virus growth, which is a characteristic, focal cytopathic effect, readily distinguishable from compound toxicity. The "active dose" of a test compound is determined as being that concentration of the compound which protects 50 percent of the cells against the cytopathic effect caused by virus growth; and the "toxic dose" is determined as being that concentration of test compound which produces compound toxicity as described above in 50 percent of the cells in cultures treated with that concentration of the compound.

The antiviral complex and the compounds of the invention inhibit the growth of rhinovirus type 2 at a concentration equal to or less than 0.25 $\mu$g./ml. without at the same time producing any visible toxic effects on the tissue culture cells at doses of at least ten times the lowest active dose.

Sirodesmin A was administered intranasally to male and female rats at a dose of 0.25 mg./kg./day for 14 days. All the rats survived and no histological abnormalities were noted on post-mortem.

When used to produce an antiviral effect in the presence of host cells, the complex or compound is administered to the host to produce a concentration in the vicinity of the virus of 0.003 to 0.25 $\mu$g./ml. Application to nasal or throat tissues at a dose of 0.01 to 0.1 mg. administered 3 to 6 times a day is appropriate. In man this is equivalent to a daily oral dose of from 2 to 20 mg. per adult person.

Thus according to a further feature of the invention there is provided a pharmaceutical composition which comprises the antiviral complex, or at least one compound of the invention, in association with a pharmaceutically acceptable diluent or carrier.

The pharmaceutical composition of the invention may be in the form of a conventional tablet, lozenge, capsule, aqueous or oily solution or suspension, emulsion, nasal drops, nasal or throat spray, aerosol or snuff, and may be manufactured by conventional techniques and incorporate conventional excipients.

Preferred compositions of the invention are those which enable the antiviral complex or compound to produce an antiviral concentration of the complex or compound in those parts of the host where rhinoviruses normally grow, for example the mucosa of the nose and throat, either by direct application of the composition to those parts or indirectly by producing a sufficient blood-level of the antiviral complex or compound after oral dosing.

Such peferred compositions for direct application are, for example, lozenges which may be dissolved slowly in the mouth, in order to bathe the mouth and associated passages with a solution of the active ingredient, and nasal sprays and throat sprays in the form of a solution of the antiviral complex or compound in an inert, pharmaceutically acceptable liquid which may be inhaled and deposited in the nasal passages and in the throat, and preferred compositions for oral dosage are, for example, tablets.

A suitable tablet or lozenge contains from .05 mg. to 5 mg. of an antiviral compound of the invention, and the normal regimen for the prophylaxis or treatment of the rhinovirus infection is one tablet 3 to 6 times per day.

A suitable nasal or throat spray contains from 0.01 to 1 mg. of an antiviral compound of the invention per ml. of solution, and for the prophylaxis or treatment of the rhinovirus infection, about 0.1 ml. of such a solution is sprayed into the nose or throat of the host 3 to 6 times per day.

The compositions of the invention may also contain other known pharmaceutically useful compounds, for example nasal decongestants, antipyretics or antiseptics.

The complex, compounds, or compositions of the invention may be used prophylactically either generally, or in particular by hosts who come, or are likely to come, into close contact with another host who has a rhinovirus infection.

Administration of the complex or of a compound or composition of the invention for the treatment of a host having a rhinovirus infection may not in many cases relieve the associated symptoms, since by the time the symptoms appear the rhinovirus infection may be fully developed, but such treatment may be useful for preventing the spread of the infection to other hosts.

The invention is illustrated but not limited by the following Examples in which Examples 6 and 16 illustrate the preparation of derivatives:

EXAMPLE 1

A nutrient medium was made up as follows:

| | |
|---|---|
| Sodium nitrate | 2.0 g. |
| Potassium dihydrogen phosphate | 1.0 g. |
| Magnesium sulphate heptahydrate | 0.5 g. |
| Potassium chloride | 0.5 g. |
| Ferrous sulphate heptahydrate | 0.01 g. |
| Dextrose ("Cerelose" brand; "Cerelose" is a Registered Trade Mark) | 50.0 g. |
| Yeast extract ("Oxoid" brand; "Oxoid" is a Registered Trade Mark) | 1.0 g. |
| Minor element concentrate (see below) | 1.0 ml. |
| Distilled water to | 1 liter |

The minor element concentrate was made up as follows:-

| | |
|---|---|
| Ferrous sulphate heptahydrate | 1.0 g. |
| Copper sulphate pentahydrate | 0.15 g. |
| Zinc sulphate heptahydrate | 1.0 g. |
| Manganese sulphate tetrahydrate | 0.1 g. |
| Potassium molybdate | 0.1 g. | were dissolved in distilled water, with the addition of sufficient concentrated hydrochloric acid to give a clear solution, and finally diluted to 1 liter with distilled water.

The nutrient medium was adjusted to pH 5.8 with 10N aqueous potassium hydroxide and then autoclaved at 10 p.s.i. for 25 minutes. *Sirodesmium diversum* C.M.I. 102519 was grown at a temperature of 25° in surface culture in 90 Thompson bottles each containing 1 liter of the nutrient medium. The product was harvested after 35 days and the culture filtrate (70 liters, pH~6.5) was extracted with toluene (2 × 14 liters). The combined toluene extracts were dried with anhydrous sodium sulphate, and then evaporated at 60°C./20 mm. The residue (7.1 g.) was washed with petroleum ether (b.p. 60°–80°C., 4 × 25 ml.) and the washings were discarded to give the antiviral complex.

EXAMPLE 2

The antiviral complex from two runs of Example 1 were pooled (6.52 g.) and then split into 2 equal portions. Each portion was fractionated separately by dry-column chromatography, each column being prepared as follows:-

A 2 liter flask containing silica gel (900 g., Hopkins and Williams Ltd., "Silica Gel M.F.C.") and water (100 ml.), was rotated at room temperature for 2 hours. Diethyl ether: ethyl acetate (3:2) (115 ml.) was added and the flask rotated for a further 3 hours. Finally, the silica gel was packed in a nylon sheath to give a dry column 90 cm. × 4 cm.

The complex was added to the top of the column in the minimum volume of ether: ethyl acetate (3:2) and the column was developed with the same solvent mixture until the solvent front reached the base of the column. Each column was excised into six equal sections and equivalent sections from the two columns were combined, then eluted with ethyl acetate: methanol (97:3) (3 × 500 ml.). Evaporation of the solvents yielded six fractions; fraction 1 was the least polar and fraction 6 was the most polar. Fractions 1–3 were discarded; fraction 4 contained Sirodesmins A and C together with less polar material, fraction 5 contained Sirodesmins A, B and C together with unwanted material, fraction 6 contained Sirodesmin B together with baseline material.

Fractions 4–6 were separated further as detailed below by preparative thin layer chromatography on silica gel G.F. (each plate 20 × 40 × 0.1 cm.). Two solvent mixtures were used for development:- Solvent I was ethyl acetate: toluene (2:1), solvent II was formic acid: methanol: chloroform (1:4:95). The separated material was recovered by elution of the appropriate bands with ethyl acetate: methanol (97:3).

T.l.c. separation of dry column fraction 4 (780 mg. 8 plates, solvent I) gave fraction (i) (92 mg., mainly Sirodesmin A) and fraction (ii) (165 mg., mainly Sirodesmins A and C). Further t.l.c. separation of fraction (i) (1 plate developed twice, solvent II) gave fraction (iii) (43 mg., Sirodesmin A). Further t.l.c. separation of fraction (ii) (2 plates developed twice, solvent II) gave faction (iv) (36.4 mg., Sirodesmin A and a trace of Sirodesmin C) and fraction (v) (65 mg., Sirodesmin C contaminated with slight traces of Sirodesmins A and B).

T.l.c. separation of dry column fraction 5 (716 mg., 8 plates, solvent I) gave fraction (vi) (296 mg., mainly Sirodesmins A and C) which was separated further (6 plates, solvent II) to give fraction (vii) (63.4 mg., mainly Sirodesmin A) and fraction (viii) (146 mg., mainly Sirodesmin C). Fractions (iv) and (Vii) were combined, then further separated (2 plates developed twice, solvent II) to give fraction (ix) (37 mg., Sirodesmin A). Fractions (iii) and (ix) were combined and dissolved in benzene (2 ml.), and petroleum ether (b.p. 60°–80°C.) was then added dropwise to the stirred solution to precipitate solid Sirodesmin A (68 mg.).

Fraction (viii) was further separated (1 plate developed twice, solvent II) to give a fraction (x) (68 mg., Sirodesmin C contaminated with slight traces of Sirodesmins A and B). Fractions (v) and (x) were combined and dissolved in ethyl acetate (2 ml.) and the solid Sirodesmin C (60 mg.) was recovered by precipitation with petroleum ether.

T.l.c. separation of dry column fraction 6 (6 plates, solvent II) gave fraction (xi) (193 mg., an oil, Sirodesmin B) which on treatment with benzene: petroleum ether yielded solid Sirodesmin B (113 mg.).

EXAMPLE 3

The antiviral complex (2.5 g.), obtained from a 90 liter fermentation, in dry pyridine (50 ml.), was treated with thionyl chloride (5.0 ml.) for 15 minutes at 0°C., then added to iced-water (500 ml.) and left for an additional 15 minutes. The mixture was adjusted to pH 2 with 2N. sulphuric acid, then extracted with chloroform (3 × 500 ml.). The extracts were dried over sodium sulphate, then concentrated to an oil (1.43 g.) which was applied to a "dry column" of silica gel (430 g.) prepared as follows:-

A 2 liter flask containing silica gel (1 kg., Hopkin and Williams Ltd., Silica Gel M.F.C.) and water (120 ml.), was rotated at room temperature for 2 hours. Ethyl acetate: toluene (2:1) (112.5 ml.) was then added and the flask rotated for a further 3 hours. The column was developed with ethyl acetate: toluene (2:1), then excised into 9 portions each of which was eluted with ethyl acetate: methanol (97:3) (3 × 500 ml.). The fractions containing Sirodesmin A were pooled, then separated by t.l.c. (silica gel G.F., ethyl acetate: toluene (2:1) ) to give pure Sirodesmin A as an oil (218 mg.).

A second batch of petroleum washed toluene extract from a 90 liter fermentation was processed similarly and the two samples of Sirodesmin A (total 505 mg.) were pooled and dissolved in benzene (5 ml.). Solid Sirodesmin A (385 mg.) was pecipitated from the solution by dropwise addition of petroleum ether (b.p. 60°–80°C.).

EXAMPLE 4

Sirodesmin B (50 mg.) in dry pyridine (1.0 ml.) was treated with thionyl chloride (0.1 ml.) for 12 minutes at 0°C., then added to iced-water (25 ml.) and left for 15 minutes. The solution was adjusted to pH 2 with 2N.sulphuric acid, then extracted with chloroform (3 × 20 ml.). The extracts were dried over sodium sulphate, then concentrated to an oil (29.4 mg.) which was essentially Sirodesmin A but contained traces of Sirodesmin B and C. The crude product was purified by preparative t.l.c. on silica gel G.F. (solvent, formic acid: methanol: chloroform, 1:4:95) to yield Sirodesmin A as an oil (12.5 mg.).

EXAMPLE 5

Sirodesmin C (5.0 mg.) in dry pyridine (0.1 ml.) was treated with thionyl chloride (0.01 ml.) for 10 minutes at 0°C., then added to iced-water (5 ml.) and left for 15 minutes. The solution was adjusted to pH 2 with 2N.sulphuric acid, then extracted with chloroform (3 × 5 ml.). The extracts were dried over sodium sulphate, then concentrated to yield Sirodesmin A as an oil (4.3 mg.).

EXAMPLE 6

Sirodesmin A (250 mg.) in dry pyridine (9.5 ml.) was reacted with acetic anhydride (6.25 ml.) at room temperature in the absence of light for 1 week, then treated with water (1.25 ml.) for 1 hour at 5°C. The mixture was adjusted to pH 2 with 2N. sulphuric acid, then diluted with water (25 ml.) and extracted with ethyl acetate (4 × 50 ml.). The extracts were dried over sodium sulphate, then concentrated to an oil (280 mg.) which was purified by preparative silica gel t.l.c. (solvent:- formic acid: methanol: chloroform, 1:4:95). The major component so obtained was recrystallised twice from ethyl acetate: petroleum to give Sirodesmin A bis-acetate as pale yellow needles (127 mg.), m.p. 186°–189°C.

vested after 28 days and the filtrate (70 l.) was extracted with chloroform (2 × 14 l.) dried over anhydrous sodium sulphate and evaporated under reduced pressure to give the antiviral complex. Toluene, methanol, chloroform and water were shaken together in the ratio by volume of 9:9:4:4 respectively to give a 2-phase system (upper and lower). The antiviral complex (15 g.) was dissolved in the lower phase (300 ml.) and this solution and then two further portions (300 ml.) of lower phase were shaken with upper phase (2 × 100 ml.). The combined lower phases (900 ml.) were evaporated to dryness and the residue was dissolved in the lower phase (100 ml.) of a second two phase system prepared by shaking light petroleum (b.p. 60°–80°C.), toluene, methanol and water in the ratio by volume of 2:3:4:1 respectively. This solution and a second portion of the lower phase of the second two-phase system (100 ml.) were shaken successively with upper phase (2 × 100 ml.) and the combined lower phases (200 ml.) were evaporated to dryness. The residue (10 g.) was chromatographed on deactivated silica gel (850 g.) [prepared by treating portions of silica gel (250 g.) with water (30 ml.) and mixing thoroughly in a screw-capped bottle by rolling on a ball mill] and the fractions which were eluted were further purified by multiple preparative thin layer chromatography on silica gel G.F. in which after each run, the relevant material was isolated from the plate in the usual way and reapplied to a further plate before being developed. The results of the chromotography are displayed in the following Table:-

| Column Chromatography | | | T.l.c. Chromatography | Compound Isolated |
|---|---|---|---|---|
| Fraction No. | Developing Solvent | | Developing Solvent(s) | |
| | % Ethyl acetate in toluene | Volume (l) | | |
| 1 | 20 | 4.5 | | |
| 2 | 30 | 2.0 | | |
| 3 | 30 | 1.7 | a,b | Sirodesmin G |
| 4 | 40 | 3.6 | b,b,b,c | Sirodesmin F |
| | | | b,b,b,b,c,c,b,c | Sirodesmin E |
| | | | b,a,b | Sirodesmin D |
| 5 | 40 | 1.0 | b.a | Sirodesmin H |
| 6 | 50 | 1.4 | b | Sirodesmin A |
| 7 | 50 | 5.0 | b,b | Sirodesmin A |
| | | | d,b* | Sirodesmin C |
| 8 | 50 | 1.4 | | |
| 9 | 100 | 1.8 | | |
| 10 | 100 | 5.6 | ** | Sirodesmin B | a Toluene: ethyl acetate 1:2
b Chloroform: methanol: formic acid 95:4:1
c Chloroform: ethyl acetate 1:1
d Chloroform: methanol 95:5
*Final purification using solvent b as this inhibits the disproportionation reaction during chromatography of Sirodesmin C into a mixture of Sirodesmins A and B.
**Purified on a column of 225 g. of deactivated silica developed with chloroform.

EXAMPLE 7

A solution of Sirodesmin A (50 mg.) and sulphur (15 mg.) in pyridine (2 ml.) was kept at room temperature in the dark for 24 hours, then evaporated to dryness at 35°C. Sirodesmins A, B and C were obtained by preparative thin layer chromatography of the residue (1 plate silica gel GF, 40 × 20 × 0.1 cm.; solvent system-ethyl acetate: toluene, 2:1).

EXAMPLE 8

A culture grown as described in Example 1 was har-

EXAMPLE 9

To a solution of the purified antiviral complex (11 g.) (prepared as described in Example 8 by solvent partition) in pyridine (30 ml.) was added a cold solution of SO₂ in pyridine (prepared by bubbling SO₂ into 51 ml. of pyridine until the volume was 62 ml.). After ½ hour at room temperature, the reaction mixture was poured onto ice and the pH adjusted to 2 with 2NHCl (410 ml.). The mixture was extracted with chloroform, and the chloroform washed, dried and evaporated to give a residue (8.9 g.) which was chromatographed on deactivated silica gel, with the following results:-

| Fraction No. | Development % Ethyl acetate in toluene | Volume (l) | Fraction Weight (g) |
|---|---|---|---|
| 1 | 40 | 1.1 | |
| 2 | 40 | 1.6 | 1.2 |
| 3 | 40 | 0.5 | |
| 4 | 40 | 0.9 | 0.88 |
| 5 | 40 | 1.1 | |
| 6 | 70 | 1.6 | 2.5 |

Fraction 2 was purified by preparative thin layer chromatography on silica gel GF, first using $CHCl_3$: $CH_3OH$: HCOOH 95:4:1 as solvent to separate the high and low $R_f$ fractions. The low $R_f$ fractions were further purified by preparative t.l.c. using ethyl acetate: $CHCl_3$ 7:3 as solvent to give Sirodesmin J.

The high $R_f$ fractions were purified by preparative t.l.c. using $CHCl_3$: $CH_3OH$: HCOOH 95:4:1 as solvent followed by toluene: ethyl acetate 1:2 as solvent to give Sirodesmin G.

Fractions 5 and 6 were combined and chromatographed on a column of deactivated silica gel (288 g.) with chloroform to give Sirodesmin A.

EXAMPLE 10

The residue from the chloroform extract described in Example 9 (4.46 g.) was dissolved in methanol (400 ml.) containing concentrated HCl (4 ml.) and the solution allowed to stand 40 hours at room temperature. The solution was evaporated to 35 ml. and water (35 ml.) added. the mixture was extracted with a mixture of light petroleum (b.p. 60°–80°C.) and toluene (2:3, 2 × 20 ml.) and these extracts and some unsoluble matter discarded. The remaining aqueous phase was extracted with chloroform, the chloroform evaporated and the residue divided into equal portions.

One portion (1.15 g.) was chromatographed on deactivated silica gel as follows:-

| Fraction No. | Solvent | Solvent Volume (ml.) |
|---|---|---|
| 1 | Toluene: Ethyl acetate 1:1 | 370 |
| 2 | $CHCl_3$ | 480 |
| 3 | $CHCl_3$ | 870 |

The residue from fraction 3 was recrystallised from acetone to give Desacetylsirodesmin A, m.p. 199°–201°C.

The other portion of crude product was crystallised from acetone to give Desacetylsirodesmin A, m.p. 198°–201°C.

EXAMPLE 11

A nutrient medium made up as described in Example 1 was adjusted to pH 5.6 with 10N aqueous potassium hydroxide and then autoclaved at 10 p.s.i. for 25 minutes. Sirodesmium diversum C.M.I. 102519 was grown at a temperature of 25°C. in 500 ml. conical flasks, each containing 150 mls. of the medium, on a rotary shaker. After 4 days, 12 mls. of the broth was used to innoculate each of a further number of shake flasks containing the same amount of the same medium. After 12 days under the same conditions of growth the flasks were harvested. The filtrate (50 ml.) was adjusted to pH 6.0 and extracted twice with half its volume of chloroform. The combined extracts were evaporated to give the antiviral complex.

EXAMPLE 12

Sirodesmium diversum C.M.I. 102519 was grown at a temperature of 25°C. in 2 liter conical flasks on a rotary shaker, each flask containing 1 liter of a nutrient medium made up as described in Example 11. After three days, 3 liters of the broth was used to innoculate 30 liters of a nutrient medium made up as follows:-

| | |
|---|---|
| Glycerol | 40.0 g. |
| Sodium nitrate | 2.21 g. |
| Potassium dihydrogen phosphate | 5.0 g. |
| Magnesium sulphate heptahydrate | 1.0 g. |
| Distilled water to 1.0 l. | |

The nutrient medium was autoclaved at 15 p.s.i. for 25 minutes. The pH of the medium was not adjusted, and the pH of the sterilized medium was 4.9.

The medium was contained in a glass and stainless steel fermenter of 40 liters capacity. Sterile air was supplied at 15 l./minute and the contents agitated by a 4-bladed turbine driven at 380 r.p.m., no baffling being used. An antifoam agent, propylene glycol 750, was added when required.

After 15 days, the pH of the broth was 6.7. The pH was adjusted tp 6.0, the filtrate from the broth was extracted with chloroform, and the chloroform evaporated to give the antiviral complex.

EXAMPLE 13

A solution of Sirodesmin A (0.083 g.) in methanol (100 ml.) containing concentrated HCl (1 ml.) was allowed to stand in the dark at room temperature for 4 days, then evaporated to dryness below 20°C. Methanol was added to the residue and the solution was evaporated to remove the last traces of HCl. The residue was purified by preparative thin layer chromatography on silica gel GF using $CHCl_3$: $CH_3OH$: HCOOH 95:4:1 as solvent to give Desacetylsirodesmin A, m.p. 198°–201°C. on recrystallisation from ethyl acetate/petroleum ether.

EXAMPLE 14

A solution of Sirodesmin A (0.15 g.) and triphenyl phosphine (0.078 g.) in chloroform was allowed to stand 4 hours at room temperature and then evaporated to dryness. The residue was purified by preparative thin layer chromatography on silica gel GF using $CHCl_3$: $CH_3OH$: HCOOH 95:4:1 as solvent to give Sirodesmin monosulphide, obtained as a gel which dried as a colourless powder by precipitating it from an ethyl acetate solution with petroleum ether.

EXAMPLE 15

Sirodesmin G (0.1 g.) was dissolved in methanol (100 ml.) containing concentrated HCl (1 ml.) and the solution was allowed to stand for 3 days at ambient temperature in the dark. The solvent was distilled off and the residue purified by preparative thin layer chromatography on silica gel GF using 5 percent methanol/chloroform as developing solvent to give Desacetylsirodesmin G, m.p. 195°–196.5°C. on recrystallisation from acetone.

EXAMPLE 16

Sirodesmin G (0.044 g.) was dissolved in a mixture of pyridine (2 ml.) and acetic anhydride (1 ml.) and the solution was allowed to stand in the dark for 9 days at room temperature. The solution was cooled in ice/salt, cold water (0.4 ml.) added and the mixture allowed to stand for 4 hours. After addition of 3N $H_2SO_4$ (60 ml.) the mixture was extracted with ethyl acetate (3 × 25 ml.) and the combined extracts washed with water (50 ml.), 5 percent $NaHCO_3$ solution (2 × 50 ml.) and again water (50 ml.). The organic layer was evaported, and the residue recrytallised from ethyl acetate/petroleum ether to give Sirodesmin G bisacetate, m.p. 159°–159.5°C.

EXAMPLE 17

An intranasal spray formulation of Sirodesmin A is made up using the following constituents:-

| | |
|---|---|
| Sirodesmin A | 6 mg. |
| Thimerosal | 2 mg. |
| Methyl p-hydroxybenzoate | 80 mg. |
| Propyl p-hydroxybenzoate | 20 mg. |
| Sodium phosphate | 500 mg. |
| EDTA disodium salt | 5 mg. |

-continued
Pyrogen-free distilled water to 100 ml.

What we claim is:

1. A compound of the formula:-

[Chemical structure: Formula I]

wherein n is 2 and either $R^1$ is acetyl and $R^2$ is hydrogen or $R^1$ and $R^2$ are both hydrogen or both acetyl.

2. Sirodesmin A having formula I set out in claim 1 wherein n is 2, $R^1$ is acetyl and $R^2$ is hydrogen.

* * * * *